United States Patent
Oka et al.

(10) Patent No.: US 7,055,540 B2
(45) Date of Patent: Jun. 6, 2006

(54) METHOD OF MOVING FLUID IN CAPILLARY CHIP

(75) Inventors: Hiroaki Oka, Hirakata (JP); Tetsuo Yukimasa, Nara (JP); Maki Katagiri, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/195,649

(22) Filed: Aug. 3, 2005

(65) Prior Publication Data

US 2005/0274423 A1 Dec. 15, 2005

Related U.S. Application Data

(63) Continuation of application No. PCT/JP2004/015453, filed on Oct. 13, 2004.

(30) Foreign Application Priority Data

Oct. 15, 2003 (JP) ............................. 2003-354655

(51) Int. Cl.
*E03B 1/00* (2006.01)
*F15C 1/00* (2006.01)

(52) U.S. Cl. .................... 137/1; 137/803; 137/828; 137/833; 204/601; 422/101

(58) Field of Classification Search ............... 137/828, 137/803, 1, 833; 204/601, 605; 422/101
See application file for complete search history.

(56) References Cited

U.S. PATENT DOCUMENTS 3,568,692 A * 3/1971 Metzger et al. ............. 137/827

(Continued)

FOREIGN PATENT DOCUMENTS

JP 08-261986 10/1996

(Continued)

OTHER PUBLICATIONS

Tashiro, K., et al. "A Particles and Biomolecules Sorting Micro Flow System Using Thermal Gelation of Methyl Cellulose Solution." Department of Electronics, Information and Communication Engineering, Department of Physics, Micro Total Analysis System 2001, pp. 471-473.

*Primary Examiner*—A. Michael Chambers
(74) *Attorney, Agent, or Firm*—McDermott Will & Emery LLP

(57) ABSTRACT

The present invention is a method of moving a fluid in a capillary using a capillary chip having a layer including a polymer composition and a capillary formed on the surface or inside of the aforementioned layer including a polymer composition, wherein the aforementioned capillary has a movement control part, and the aforementioned movement control part includes multiple and sequential opening/closing parts; the aforementioned opening/closing part blocks movement of the fluid that flows in the aforementioned capillary by increase in the volume of the aforementioned polymer composition to result in the closed state, while it permits movement of the fluid that flows in the aforementioned capillary by decrease in the volume of the aforementioned polymer composition to result in the open state; and the aforementioned method of moving the fluid includes a step (a) of switching the aforementioned multiple opening/closing parts from the open state to the closed state sequentially in a movement direction by changing the temperature of the aforementioned polymer composition in the aforementioned movement control part, thereby moving the fluid in the aforementioned capillary.

17 Claims, 10 Drawing Sheets

U.S. PATENT DOCUMENTS

| | | |
|---|---|---|
| 6,499,499 B1 * | 12/2002 | Dantsker et al. ............... 137/1 |
| 6,616,825 B1 * | 9/2003 | Frechet et al. .............. 204/605 |
| 6,887,384 B1 * | 5/2005 | Frechet et al. .............. 210/634 |

FOREIGN PATENT DOCUMENTS

| JP | 2000-514928 | 11/2000 |
|---|---|---|
| JP | 2001-165939 | 6/2001 |
| JP | 2002-036196 A | 2/2002 |
| JP | 2002-066999 A | 3/2002 |
| JP | 2002-282682 | 10/2002 |
| JP | 2003-503716 | 1/2003 |
| WO | WO 01/02737 A1 | 1/2001 |

* cited by examiner

METHOD OF MOVING FLUID IN CAPILLARY CHIP

This is a continuation application under 35 U.S.C. 111(a) of pending prior International Application No. PCT/JP2004/015453, filed on Oct. 13, 2004, which in turn claims the benefit of Japanese Application No. 2003-354655 filed on Oct. 15, 2003, the disclosures of which Applications are incorporated by reference herein. The benefit of the filing and priority dates of the International and Japanese Applications is respectfully requested.

BACKGROUND OF THE INVENTION

1. Field of the Invention

The present invention relates to a capillary chip, specifically a capillary chip having a capillary which is useful for conveniently carrying out analyses of a sample in a slight amount.

2. Description of the Related Art

In applications of micromachine techniques, minimization and integration of chemical analysis systems are in one of the most promising fields. Minimized and integrated chemical analysis systems are referred to as micro TAS (Micro Total Analysis Systems). Micro TAS is a system formed on one capillary chip, usually in an about 1 to 2 cm square, comprising a capillary to be a flow channel of a liquid that is a sample and a reagent, a reaction space and a detection space. This system has been expected to attempt saving of the sample, speeding up of the analysis, automatization of the measurement including a pretreatment, rendering the device portable, rendering the device disposable, reducing costs for the device, and the like.

For example, in analytical devices for use in medical diagnoses using blood or the like as a sample, micro TAS is extremely useful which can be conveniently used at the patient's bed side and the like, and which allows the capillary chip that is brought into contact with the sample to be disposable.

Hereafter, development of fine movement control elements such as microvalves which control opening/closing of the flow channel in the capillary chip, liquid delivery driving elements for moving a fluid in a flow channel and the like is indispensable for constructing a sophisticated system in which micro TAS is used.

In general methods of moving a fluid in a flow channel, a liquid delivery pump or a suction pump located outside of the capillary chip is used. In this type of method, due to necessity of an external pump, problems in connection with responsiveness of the control, continuous change, durability, quietness that is important in medical sites and the like are involved. Also, there is the possibility that the device may be entirely enlarged, and that leakage may occur at a junction of the capillary chip with the external pump.

In addition, a method in which a fluid in a flow channel is moved utilizing the electroosmotic flow caused by applying electrophoretic voltage to the liquid in the flow channel has been also known (for example, see JP-A No. H08-261986). According to this method, voltage is applied to the liquid in the flow channel via an electrode, therefore, electrolysis of the measurement sample or the reagent may be caused on the surface of the electrode, leading to alteration of the sample composition or reagent composition.

Further, as the aforementioned microvalve, a valve to occlude the flow channel with wax has been known (for example, see JP-T No. 2000-514928 (the term "JP-T" as used herein means a published Japanese translation of a PCT application)). However, the valve provided using wax involves problems such as limitation of possible application only to flow channels having a great diameter to some extent, adsorption of components in the liquid to the wax, difficulty in controlling rapid opening/closing, and the like.

Moreover, as other microvalve, a valve provided using a coupler has been known (for example, see JP-A No. 2001-165939). Such a valve has a function to arrest the flow of a liquid, which flows into or flows out of a liquid reservoir supplies the liquid to the flow channel, by allowing a coupler to cohere to a part of the liquid reservoir where it opens to atmospheric air and. Movement of the fluid can be recovered by removing the coupler from the cohesive state. However, according to this valve, the coupler must cohere so that airtightness is kept with the liquid reservoir, leading to necessity of complicated production and manipulation. Further, there exists a problem that the opening/closing part of the flow channel can not be optionally selected.

Also, K. Tashiro et al., "A Particles and Biomolecules sorting micro flow system using thermal gelation of methyl cellulose solution", Micro Total Analysis System 2001, p.471–473 discloses a method in which a flow channel is occluded by preparing a solution which is gelated upon irradiation with a laser, and gelating the solution in the flow channel. However, in this method, a solution which meets a particular requirement must be prepared. Furthermore, although this method can be utilized in occluding a flow channel, use in multiple times as a valve for opening/closing shall be difficult because it goes into a liquid form in its open state.

Additionally, JP-T No. 2003-503716 (the term "JP-T" as used herein means a published Japanese translation of a PCT application) discloses a method of opening/closing a flow channel in which a plug comprising a polymer material is provided in a flow channel, and alteration in the volume of this polymer material is utilized. However, there exist problems in this method that the aforementioned plug must be provided at an arbitrary position, and that opening/closing can not be executed except for the position where the plug is provided.

SUMMARY OF THE INVENTION

An object of the present invention is to provide a method of moving a fluid in a capillary in a simple manner without altering composition of a sample or a reagent in a capillary chip, and a device for controlling movement of a fluid which enables carrying out the method of moving the fluid.

In order to achieve the object described above, the present invention provides a method of moving a fluid in a capillary using a capillary chip having a layer comprising a polymer composition and a capillary formed on the surface or inside of the aforementioned layer comprising a polymer composition, wherein the aforementioned capillary has a movement control part, and the aforementioned movement control part comprises multiple and sequential opening/closing parts; the aforementioned opening/closing part blocks movement of the fluid that flows in the aforementioned capillary by increase in the volume of the aforementioned polymer composition to result in the closed state, while it permits movement of the fluid that flows in the aforementioned capillary by decrease in the volume of the aforementioned polymer composition to result in the open state; and the aforementioned method of moving the fluid comprises a step (a) of switching the aforementioned multiple opening/closing parts from the open state to the closed state sequentially in a movement direction by changing the temperature of the aforementioned polymer composition in the aforementioned movement control part, thereby moving the fluid in the aforementioned capillary. In this method, the fluid in the capillary can be moved by the simple step (a) in which the temperature of the polymer composition is merely changed.

Further, in the method of moving the fluid described above, the step (a) may be conducted repeatedly more than once. By repeating the step (a), the fluid in the movement control part shall be repeatedly pushed out. Moreover, the method may comprise after each step (a), the following steps, i.e., a step (b) of, while keeping the closed state of one or more opening/closing parts positioned from the downstream end along the movement direction, switching other opening/closing part from the closed state to the open state by changing the temperature of the aforementioned polymer composition in the aforementioned movement control part, and a step (c), following the step (b), of switching the opening/closing part from the closed state in the step (b) to the open state. In this case, the next step (a) is initiated substantially concomitantly to the step (c). According to this method, the aforementioned movement control part can function as a pump.

Further, the aforementioned method of moving the fluid may further comprise the following steps, i.e., a step (d) of blocking movement of the fluid that flows in the aforementioned capillary through changing the temperature of the aforementioned polymer composition in the aforementioned opening/closing part to turn the aforementioned opening/closing part into the closed state, and a step (e) of permitting movement of the fluid that flows in the aforementioned capillary through changing the temperature of the aforementioned polymer composition in the aforementioned opening/closing part to turn the aforementioned opening/closing part into the open state. In this case, movement of the fluid in the capillary chip can be controlled in a more complex manner by combination of the moving in the step (a) and the opening/closing in the steps (d) and (e).

As the aforementioned polymer composition, for example, any of polymer compositions can be used which increase in the volume upon elevation of the temperature, and decrease in the volume upon lowering of the temperature. Alternatively, any of polymer compositions can be used which decrease in the volume upon elevation of the temperature, and increase in the volume upon lowering of the temperature. Furthermore, combination of both also enables concomitantly controlling the open state and closed state in a complicated flow channel.

Specific examples of the aforementioned polymer composition include a polymer composition comprising a side chain-crystalline recurring unit derived from an acrylate or methacrylate ester, and a side chain-noncrystalline recurring unit derived from an acrylate or methacrylate ester.

In a construction of one mode of the aforementioned capillary chip, the aforementioned capillary is formed on the surface of the aforementioned layer, and a cover flat plate coheres on the surface of the aforementioned layer.

The aforementioned capillary chip may further comprise a fluid inlet and a fluid outlet connected to the aforementioned capillary.

The step (a) is suitably a step of heating by, for example, irradiating a laser on the aforementioned opening/closing part of the aforementioned movement control part sequentially in the movement direction. In this case, the aforementioned heating can be conducted by, for example, irradiating a laser.

In the step (b) and the step (c), the aforementioned opening/closing part may be switched from the closed state to the open state by, for example, air-cooling of the aforementioned opening/closing part.

As the aforementioned polymer composition, a polymer composition which is altered in the volume by its first order melting transition is preferably used. It is more preferred that the first order melting transition of the aforementioned polymer composition is caused at 80° C. or lower.

Cross sectional area of the aforementioned capillary may be, for example, 10000 μm$^2$ or greater and 250000 μm$^2$ or less.

The aforementioned capillary chip may be constructed to have multiple fluid inlets that are connected to the aforementioned capillary, and the aforementioned capillary has multiple opening/closing parts so as to correspond to each fluid inlet.

In addition, the present invention provides a device for controlling movement of a fluid which comprises a capillary chip attached part, a laser irradiation part and a laser control part, wherein a capillary chip can be attached to the aforementioned capillary chip attached part; the aforementioned capillary chip has a layer comprising a polymer composition, and a capillary formed on the surface or inside of the aforementioned layer comprising a polymer composition; the aforementioned capillary comprises a movement control part; the aforementioned movement control part comprises multiple and sequential opening/closing parts; the aforementioned opening/closing part blocks movement of the fluid that flows in the aforementioned capillary by increase in the volume of the aforementioned polymer composition to result in the closed state, while it permits movement of the fluid that flows in the aforementioned capillary by decrease in the volume of the aforementioned polymer composition to result in the open state; the aforementioned laser irradiation part can irradiate a laser on the capillary chip attached to the aforementioned capillary attached part; and the aforementioned laser control part can control a position where a laser is irradiated on the capillary chip attached to the aforementioned capillary attached part by the aforementioned laser irradiation part, and the aforementioned opening/closing part is switched from the open state to the closed state sequentially in a movement direction by irradiating the aforementioned opening/closing part sequentially in the movement direction thereby moving the fluid in the aforementioned capillary.

The above-described and other object, features and advantages of the present invention will be apparent from the following detailed description of preferred embodiments with reference to accompanying drawings.

DETAILED DESCRIPTION OF THE PREFERRED DESCRIPTION

The present invention will be explained below in more detail by using drawings.

First Embodiment

[Construction of Capillary Chip]

Figure 1A:
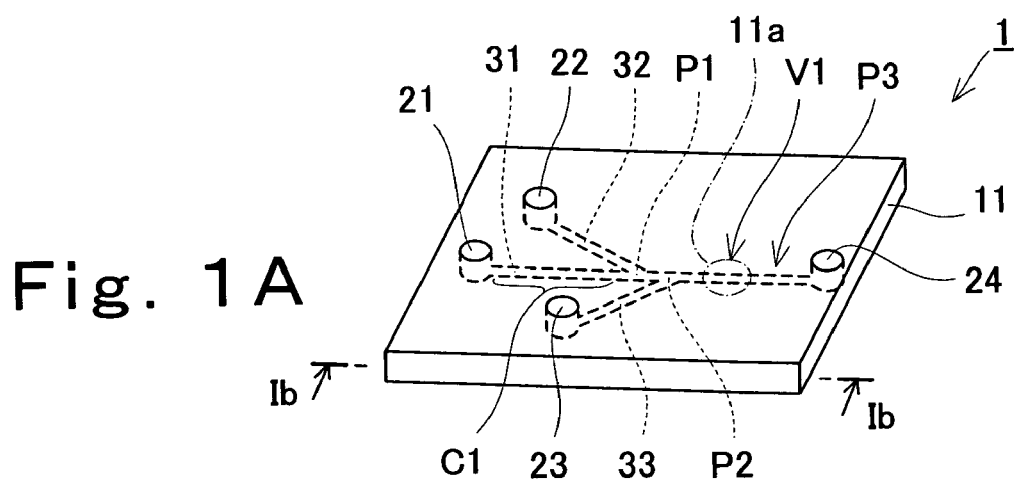
FIG. 1A is a perspective view schematically illustrating an external appearance of a capillary chip used in the first embodiment.
Figure 1B:
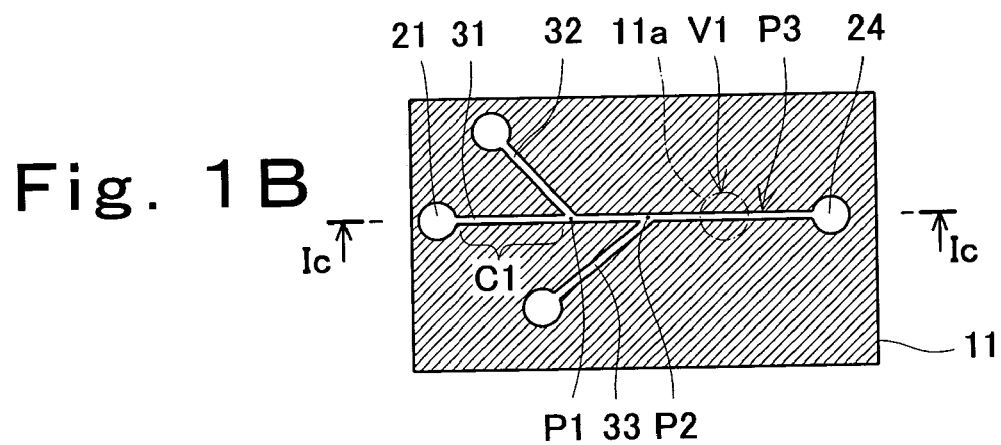
FIG. 1B is a cross sectional view showing a Ib—Ib section.
Figure 1C:
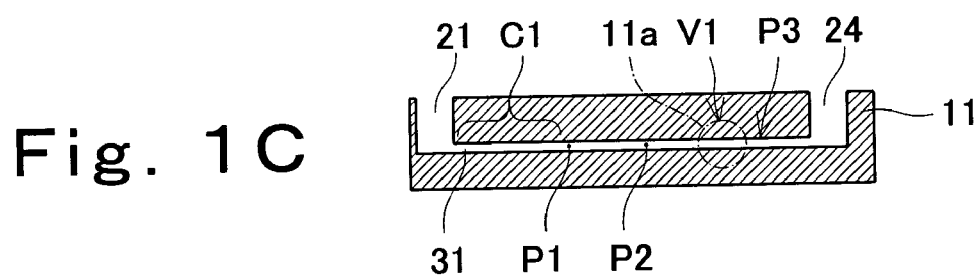
FIG. 1C is a cross sectional view showing a Ic—Ic section.

FIG. 1A is a perspective view schematically illustrating an external appearance of a capillary chip 1 used in this embodiment. FIG. 1B is a cross sectional view illustrating a Ib—Ib section in FIG. 1A; and FIG. 1C is a cross sectional view illustrating a Ic—Ic section in FIG. 1B. As shown in FIG. 1A to FIG. 1C, the capillary chip 1 comprises a substrate 11 having a rectangular plane shape on which a main flow channel 31, branch flow channels 32 and 33, a sample inlet 21, reagent inlets 22 and 23, and an outlet 24 are formed. Each of the flow channels 31, 32 and 33 is constructed with a capillary. The main flow channel 31 joins to a branch flow channel 32 at a junction P1, and joins to a branch flow channel 33 at a junction P2. The substrate 11 is placed preferably even with the ground.

The sample inlet 21 is constructed from a pore having a section of circular, which extends from the surface of the substrate 11 to the upstream end of the main flow channel 31. The reagent inlet 22 is constructed from a pore having a section of circular, which extends from the surface of the substrate 11 to the upstream end of the branch flow channel 32. The reagent inlet 23 is constructed from a pore having a section of circular, which extends from the surface of the substrate 11 to the upstream end of the branch flow channel 33. The outlet 24 is constructed from a pore having a section of circular, which extends from the surface of the substrate 11 to the downstream end of the main flow channel 31. Owing to the sample inlet 21, the reagent inlets 22 and 23, and the outlet 24, an open system of each of the flow channels 31, 32 and 33 is provided, thereby enabling to permit the fluid to move.

The main flow channel 31 has an opening/closing part V1 that controls opening/closing of the main flow channel 31 on the downstream side of the junction P2. In addition, the main flow channel 31 has a movement control part C1 having a function to move the fluid by pushing out the fluid in the flow channel toward the vicinity of the upstream end, and a function to initiate movement of the fluid by imparting a force to the fluid in the flow channel in the downstream direction.

Transverse sectional shape of the flow channels 31, 32 and 33 is not particularly limited, but may be a polygonal shape such as square or triangle, or circular, semicircular, semi-elliptic or the like. The fluid to allow movement in the capillary chip 1 should be a liquid. Cross sectional area of the flow channels 31, 32 and 33 depends on viscosity of the liquid to be moved and size of fine particles in the liquid, however, it is preferably 1 $\mu m^2$ or greater and 1000000 $\mu m^2$ or less, and more preferably 10000 $\mu m^2$ or greater and 250000 $\mu m^2$ or less. When it is less than 1 $\mu m^2$, grounds for disturbance of movement may be provided due to the fine particles, and it may be difficult to move the fluid against thus resulting surface tension. To the contrary, when the cross sectional area is greater than 1000000 $\mu m^2$, formation of multiple flow channels on the substrate 11 having a size suitable to applications in a micro chip 1 may be difficult.

Size of the substrate 11 is determined on the basis of flow channel pattern to be formed, however, for example, the thickness may be 5 mm or greater and 50 mm or less; long side may be 5 mm or greater and 50 mm or less; and short side may be 3 mm or greater and 50 mm or less.

Size of the sample inlet 21, and the reagent inlets 22 and 23 is not particularly limited as long as it is enough in size for enabling injection of a sample or a reagent by injection means such as pipette, syringe and the like. The sample inlet 21, and the reagent inlets 22 and 23 function as a liquid reservoir of the sample or the reagent depending on the size. When the size of the sample inlet 21, and the reagent inlets 22 and 23 is not sufficient as a liquid reservoir, thereto may be connected, for example, a cylindrical member to construct a liquid reservoir. Sectional shapes of the sample inlet 21, and the reagent inlets 22 and 23 are not limited to circular, but may be polygonal or the like.

[Construction of Opening/Closing Part]

As shown in FIG. 1A to FIG. 1C, the opening/closing part V1 is constructed from a peripheral part 11a of the main flow channel 31 (hereinafter, referred to as "flow channel peripheral part 11a"). The flow channel peripheral part 11a is constructed with a portion having a predetermined length and surrounding the entire circumference of the main flow channel 31 of the substrate 11. The flow channel peripheral part 11a comprises a polymer composition. In this embodiment, the flow channel peripheral part 11a constructing the opening/closing part V1 is provided as a portion surrounding the entire circumference of the main flow channel 31, however, the flow channel peripheral part 11a may also be a portion surrounding only a part of the entire circumference of the main flow channel 31. The opening/closing part V1 becomes in the open state or the closed state depending on the volume of the polymer composition. The opening/closing part V1 is turned from the open state into the closed state upon increase in the volume through changing the temperature of the polymer composition, while it is turned from the closed state into the open state upon decrease in the volume through changing the temperature of the polymer composition. The opening/closing part V1 permits movement of the liquid in the open state, and blocks movement of the liquid in the closed state. The aforementioned increase and decrease in the volume of the polymer composition is a reversible change. Because the alteration in the volume of the polymer composition is a reversible change, the control of opening/closing that is free from limitation of frequency is enabled.

As the polymer composition, any one of polymer compositions which increase in the volume upon elevation of the temperature and decrease in the volume upon lowering of the temperature, or any one of polymer compositions which decrease in the volume upon elevation of the temperature and increase in the volume upon lowering of the temperature can be used. The polymer composition as in the former type is available from Nitta Corporation, under the trade name of Intelimer®, Cool off. The polymer composition as in the latter type is available from Nitta Corporation, under the trade name of Intelimer®, Warm off. Either one is a polymer composition having a sheet form. As the aforementioned polymer composition, a polymer composition is preferably used which causes primary melting transition in a particular temperature range. Then, alteration in the volume due to the first order melting transition is utilized in controlling the opening/closing. Alteration in the volume due to the first order melting transition is preferred because a great alteration in the volume upon changes in the temperature is achieved, thereby facilitating binary control of the opening/closing of the opening/closing part V1. Herein, the temperature range in which the aforementioned polymer composition causes first order melting transition is referred to as "melting temperature range". When a polymer composition which causes the first order melting transition is used, opening/closing of the opening/closing part V1 is controlled by changing the temperature from a lower temperature than the melting temperature range into a higher temperature than the melting temperature range, or by changing the temperature from a higher temperature than the melting temperature range into a lower temperature than the melting temperature range.

It is preferred that the melting temperature range of the polymer composition is as narrow as possible because change in the temperature required for controlling the opening/closing may be small, thereby enabling rapid control of the opening/closing. Preferably, a polymer composition that exhibits the difference between the highest temperature and the lowest temperature in the melting temperature range is 15° C. or less is used. Furthermore, a polymer composition which causes the first order melting transition within a temperature range that does not result in degeneration of the fluid is preferred. Also, a polymer composition whose temperature within the melting temperature range is higher than the solidifying point of the fluid and is lower than the boiling point of the same may be used because the temperature of the fluid adjacent to the opening/closing part V1 is affected by the temperature of the opening/closing part V1. Preferred melting temperature range may vary depending on type of the fluid which is moved, however, for example, a polymer composition whose temperature within the melting temperature range is 30° C. or greater and 80° C. or less can be used.

As the polymer composition described above; a temperature sensitive polymer composition described in JP-A No. 2002-322448, U.S. Pat. No. 5,156,911 and U.S. Pat. No. 5,387,450 can be used. Specifically, a temperature sensitive polymer composition comprising a side chain-crystalline recurring unit derived from an acrylate or methacrylate ester, and a side chain-noncrystalline recurring unit derived from an acrylate or methacrylate ester can be used. More specifically, a temperature sensitive polymer composition comprising hexadecyl acrylate as a side chain-crystalline recurring, and hexyl acrylate as a side chain-noncrystalline recurring unit can be used.

Further, a polymer composition which increases in the volume upon changing from the temperature lower than the melting temperature range to a higher temperature than the melting temperature range and decreases in the volume upon changing from the temperature higher than the melting temperature range to a lower temperature than the melting temperature range, and whose temperature within the melting temperature range is higher than room temperature (25° C.) may be preferably used. When such a polymer composition is used, the opening/closing part V1 is in the open state at room temperature, while it is turned into the closed state by heating, which is then turned into the open state by allowing to stand, i.e., by air cooling. In general, switching from the open state to the closed state requires more rapidness than switching from the closed state to the open state. For example, heating with a laser is suited for controlling the switching from the open state to the closed state, because it can achieve topical change of the temperature rapidly.

When a laser is used as heating means, any kind of laser may be selected such as gas laser, solid laser or semiconductor laser, as long as it has a necessary heating capacity. The laser is not limited as long as it emits a light having a wavelength that is suitable for heating the flow channel peripheral part 11a comprising the polymer composition, which is a target of the heating. For example, any one which emits a light having a wavelength of 1450 nm to 1490 nm by an IR laser can be used. The heating temperature may be controlled by output of the laser and irradiation time period.

[Method of Controlling Opening/Closing of Opening/Closing Part]

Method of controlling opening/closing of the opening/closing part V1 will be explained. In this embodiment, an opening/closing part V1 which is in the open state at a temperature lower than Ta, and is in the closed state at a temperature higher than Tb is explained. In addition, Ta is lower than Tb (Ta<Tb), and Ta is higher than room temperature (25° C.) (Ta>room temperature). Hereinafter, a case in which a laser is used as heating means, while air cooling is used as cooling means is explained.

Figure 2A:
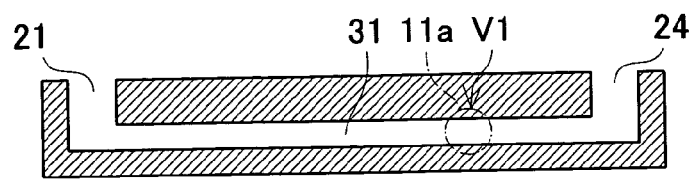
FIGS. 2A and 2B are each a cross sectional view schematically illustrating a method of controlling opening/closing of an opening/closing part.
Figure 2B:
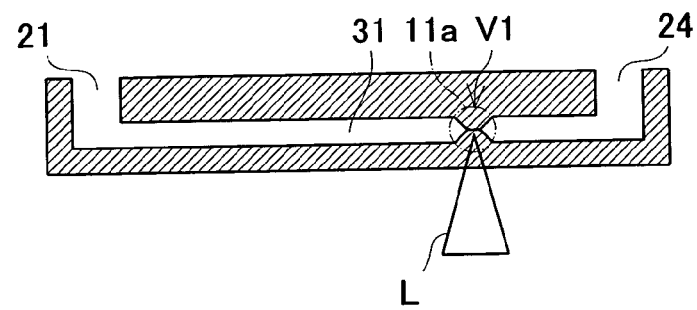

FIGS. 2A and 2B are each a cross sectional view schematically illustrating the open state (a) and the closed state (b) of the opening/closing part V1 in the same section as that in FIG. 1C. The opening/closing part V1 is in the open state at room temperature as shown in FIG. 2A. In this state, a laser light in a beam state (hereinbelow, may be also referred to "laser beam") L is irradiated on the opening/closing part V1. Thus, the opening/closing part V1 is topically heated to elevate the temperature from the room temperature upto a temperature higher than Tb. Then, the volume of the polymer composition of the flow channel peripheral part 11a is increased, however, the volume of a part other than the flow channel peripheral part 11a of the substrate 11 is unchanged. Therefore, the flow channel peripheral part 11a expands in a direction to narrow down the flow channel, thereby turning the opening/closing part V1 from the open state shown in FIG. 2A into the closed state shown in FIG. 2B. When heating of the opening/closing part V1 is continued to keep the opening/closing part V1 at a temperature higher than Tb, the closed state shall be maintained. To the contrary, when heating of the opening/closing part V1 is stopped followed by leaving to stand, the opening/closing part V1 is cooled from the temperature higher than Tb down to room temperature that is lower than Ta. Accordingly, the volume is reduced, thereby turning from the closed state shown in FIG. 2B into the open state shown in FIG. 2A.

Next, a case in which a polymer composition is used which decreases in the volume by heating and increases in the volume by cooling is explained. In this embodiment, an opening/closing part V1 which is in the open state at a temperature higher than Tc, and is in the closed state at a temperature lower than Td is explained. In addition, Td is lower than Tc (Td<Tc), and Tc is lower than room temperature (25° C.) (Tc<room temperature). At room temperature, the opening/closing part V1 is in the open state as shown in FIG. 2A. In this state, the opening/closing part V1 is cooled. Thus, the opening/closing part V1 is topically cooled to lower the temperature from the room temperature down to a temperature lower than Td. Then, the volume of the polymer composition of the flow channel peripheral part 11a is increased, however, the volume of a part other than the flow channel peripheral part 11a of the substrate 11 is unchanged. Therefore, the flow channel peripheral part 11a expands in a direction to narrow down the flow channel, thereby turning the opening/closing part V1 from the open state shown in FIG. 2A into the closed state shown in FIG. 2B. When cooling of the opening/closing part V1 is continued to keep the opening/closing part V1 at a temperature lower than Td, the closed state shall be maintained. To the contrary, when cooling of the opening/closing part V1 is stopped followed by leaving to stand, the opening/closing part V1 is warmed from the temperature lower than Td up to room temperature that is higher than Tc. Accordingly, the volume is reduced, thereby turning from the closed state shown in FIG. 2B into the open state shown in FIG. 2A.

[Construction of Movement Control Part]

FIG. 3A to FIG. 3F are a partial cross sectional view schematically illustrating a procedure of controlling the movement control part C1 in the same section as that in FIG. 1C.

Figure 3A:
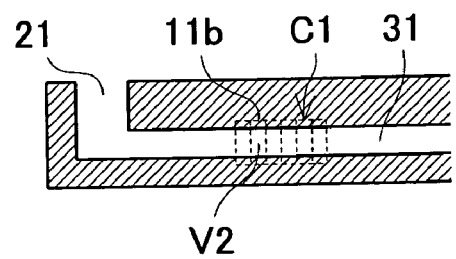
FIGS. 3A to 3F are each a cross sectional view schematically illustrating a method of moving a fluid in a movement control part.

As shown in FIG. 3A, the movement control part C1 is constructed from a peripheral part 11b of a main flow channel 31 (hereinafter, referred to as "flow channel peripheral part 11b"). The flow channel peripheral part 11b is constructed with a portion having a predetermined length and surrounding the entire circumference of the main flow channel 31 of the substrate 11. The aforementioned flow channel peripheral part 11b comprises a polymer composition, and is constructed with multiple adjacent opening/closing parts for controlling movement V2 capable of controlling similarly to the control of opening/closing by the opening/closing part V1 as described above. In this embodiment, the flow channel peripheral part 11b is provided as a portion surrounding the entire circumference of the main flow channel 31, however, the flow channel peripheral part 11b may also be a portion surrounding only a part of the entire circumference of the main flow channel 31. Preferable material as the polymer composition to form the movement control part C1 is similar to the material described in explanation of the opening/closing part V1.

[Method of Control in Movement Control Part]

Figure 3B:
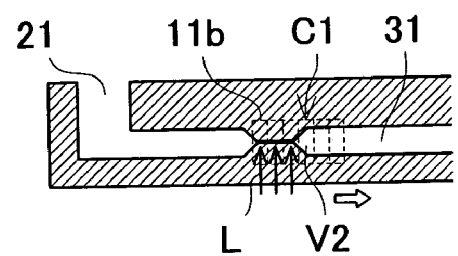
Figure 3C:
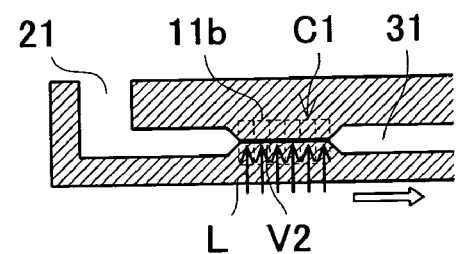

First, a method of liquid delivery of the liquid in the flow channel 31 using the movement control part C1 will be explained. Because the method of controlling the opening/closing of each opening/closing part for controlling movement V2 is similar to the method of controlling the aforementioned opening/closing part V1, the explanation is omitted. As shown in FIG. 3A to FIG. 3C, each opening/closing part for controlling movement V2 of the movement control part C1 in a state filled with a liquid is turned into the closed state by irradiating a laser beam L to heat sequentially from the upstream side of the movement direction (sample inlet 21 side) to the downstream side of the movement direction (outlet 24 side (see, FIGS. 1A to 1C)). Accordingly, the liquid is pushed out from the upstream side toward the downstream side, thereby capable of allowing the liquid to move in the flow channel 31. Also, it may depend on viscosity and the like of the liquid, it is possible to impart a force in a downstream direction to the liquid by pushing out as described above, thereby initiating movement. Moreover, it is also possible to control the flow rate by regulating the velocity of the pushing out. Additionally, through repeating the procedure of pushing out as described above, the movement control part C1 functions as a pump thereby capable of allowing the liquid in the main flow channel 31 to move.

Method of controlling to allow the movement control part C1 to function as a pump is explained below with reference to FIG. 3A to FIG. 3F. In the movement control part C1, each opening/closing part for controlling movement V2 is in the open state at a temperature lower than Ta, while it is in the closed state at a temperature higher than Tb. In addition, Ta is lower than Tb (Ta<Tb), and Ta is higher than room temperature (25° C.) (Ta>room temperature). Hereinafter, a case in which a laser is used as the heating means, while air cooling is used as the cooling means is explained.

Figure 3D:
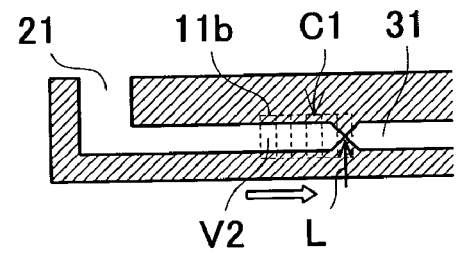
Figure 3E:
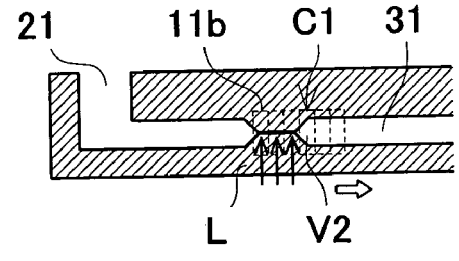
Figure 3F:
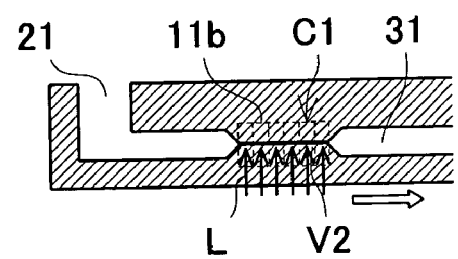

In the main flow channel 31 filled with a liquid injected from the sample inlet 21, the state in which all the opening/closing parts for controlling movement V2 are in the open state (FIG. 3A) is turned into the closed state by irradiating a laser beam L to heat each opening/closing part for controlling movement V2 sequentially from the upstream side to the downstream side (FIG. 3B), and finally, the opening/closing part for controlling movement V2 at the downmost stream is turned into the closed state (FIG. 3C). In the step shown in FIGS. 3B and 3C, the liquid within the movement control part C1 is pushed out. Thereafter, the movement control part C1 is filled with a liquid by keeping the opening/closing part for controlling movement V2 at the downmost stream to be in the closed state, and turning other opening/closing part for controlling movement V2 into the open state (FIG. 3D). Thereafter, concomitant with turning the opening/closing part for controlling movement V2 at the downmost stream into the open state, each opening/closing part for controlling movement V2 of the movement control part C1 is turned into the closed state by irradiating a laser beam L to heat sequentially from upstream side to the downstream side (FIG. 3E), and finally, the opening/closing part for controlling movement V2 at the downmost stream is turned into the closed state (FIG. 3F). In the step shown in FIGS. 3E and 3F, the liquid within the movement control part C1 is pushed out. Through repeating the control as described above, the movement control part C1 functions as a pump.

As a matter of course, opening/closing of each opening/closing part for controlling movement V2 in the movement control part C1 may be controlled alone to allow it to function as an opening/closing part for switching blocking/permission of movement of a fluid.

[Method of Using Capillary Chip]

In FIG. 1A to FIG. 1C, the capillary chip 1 can be used, for example, as follows. A sample is injected into the sample inlet 21, and a first reagent is injected into the reagent inlet 22. A reagent flow that moves in the branch flow channel 32 joins a sample flow that moves in the main flow channel 31 at the junction P1 to give a mixed flow. Then, the sample and the first reagent are mixed downstream of the junction P1, thereby causing a reaction.

Further, a second reagent is injected into the reagent inlet 23 at the appropriate time. A reagent flow that moves in the branch flow channel 33 joins the aforementioned mixed flow at the junction P2. The sample and the second reagent are mixed downstream of the junction P2, thereby causing a reaction. An arbitrary analysis is carried out at a position P3 of the main flow channel 31 where the reaction is completed. Analysis of the sample can be executed by conducting detection of the reaction solution with an optical detection method such as, for example, a photothermal conversion process, a fluorescent process, an extinction process, a chemical luminescent process or the like. Alternatively, the sample can be also analyzed by observing the reaction solution with a microscope.

Time period of the reaction of the sample with the first reagent or the second reagent can be adjusted by making the opening/closing part V1 in the closed state. In addition, movement of the liquid in the flow channel can be accelerated by carrying out the control of movement as described above in the movement control part C1.

In case where necessary detection can be conducted by allowing the sample and the reagent to react, without need of separation, such as biochemical examination items, sequential treatment is enabled in a consistent flow channel using the capillary chip 1 throughout from mixing, reaction and then to detection.

Examples of the sample which may be used in this embodiment include biological samples such as blood, spinal fluid, saliva, urine and the like. When such a biological sample is used, any biological component included in the blood, spinal fluid, saliva or urine; any biological component derived from an organ, a tissue or mucosa; a protein, DNA, RNA, allergen of a mycobacterium/myocardium or virus which may be a source of infection, any of various antigens may be a target substance of the detection.

[Other Construction]

The flow channel in the capillary chip 1 comprises a flow channel with the principal aim of transfer of the reagent or the sample (from upstream end to junction P1 of the main flow channel 31; branch flow channels 32 and 33), a flow channel with the principal aim of mixing of the reagent and the sample (from junction P1 to junction P2 of the main flow channel 31), and a flow channel with the principal aim of mixing of the reagent and the sample, and detection of the reaction fluid (from junction P2 to downstream end of the main flow channel 31). Construction of the flow channels is not limited to that demonstrated in this embodiment, but may be designed depending on the intended usage thereof.

The flow channel in the capillary chip 1 may comprise only a flow channel part with the principal aim of single manipulation (for example, sampling in a certain amount, transfer of sample or reagent, or the like), however, combination of flow channels with the principal aim of each different manipulation as described above may be accepted. Accordingly, a device allowing for not a mere qualitative analysis but an advanced analysis accompanied by a quantitative analysis can be constructed.

Additionally, in the construction of the flow channel, for example, a form having one flow channel to which other flow channel is joined (the from depicted in FIG. 1A to 1C), or a form having multiple flow channels joined to single flow channel at one site may be involved as a form of the flow channel with the principal aim of mixing or diluting the sample and the reagent. Formation of one flow channel through joining to single flow channel other flow channel or multiple flow channels enables to conduct mixing manipulation or dilution manipulation owing to the flow channel form alone. Moreover, alteration in flow rate of the liquid from the flow channel to be joined enables mixing or dilution of the sample and the reagent at a varying rate.

Examples of planar shape of the flow channel part where the liquid is homogenized include linear shape, curved shape such as tortuous or spiral, and the like. Further, a construction in which mixing and reaction of the sample and the reagent can readily proceed may be achieved by making the construction to provide a reaction part having a greater volume with respect to a unit length in the movement direction than other part in the flow channel (second Embodiment described later). Also, contrary to the above mode, split flow can be provided by constructing a flow channel diverged into numerous arms from one flow channel (branching a flow channel).

Further, in addition to such designing of the flow channel, control of timing of dilution, reaction with other reagent or the like can be executed by constructing to include the opening/closing part or the movement control part at a desired position.

In this embodiment, a capillary chip having each flow channels 31, 32 and 33 formed on the substrate 11 is used, however, the capillary chip to which the present invention can be applied is not limited thereto but, for example, each of the flow channels 31, 32 and 33 may be formed on a cylindrical substrate body.

Even though a capillary chip having a flow channel constructed with a groove having an open upper face is used, the control of opening/closing, or the control of movement as described above can be executed. However, as in this embodiment, to use a capillary chip constructed from a capillary comprising a polymer composition surrounding the entire circumference of each flow channel is more preferred in light of effective execution of the control of opening/closing and the control of movement.

Additionally, provided that the sample and the reagent are not adversely affected, periphery of the through-hole 21 constructing the sample inlet is heated to reduce the volume of the through-hole 21, and the fluid may be passed so that it is flushed from the sample inlet consisting of the through-hole 21 out to the main flow channel 31. When a polymer composition that increases in the volume upon cooling is used, as a matter of course, periphery of the through-hole 21 constructing the sample inlet is cooled to reduce the volume of the through-hole 21.

[Device for Controlling Movement of Capillary Chip]

Figure 9:
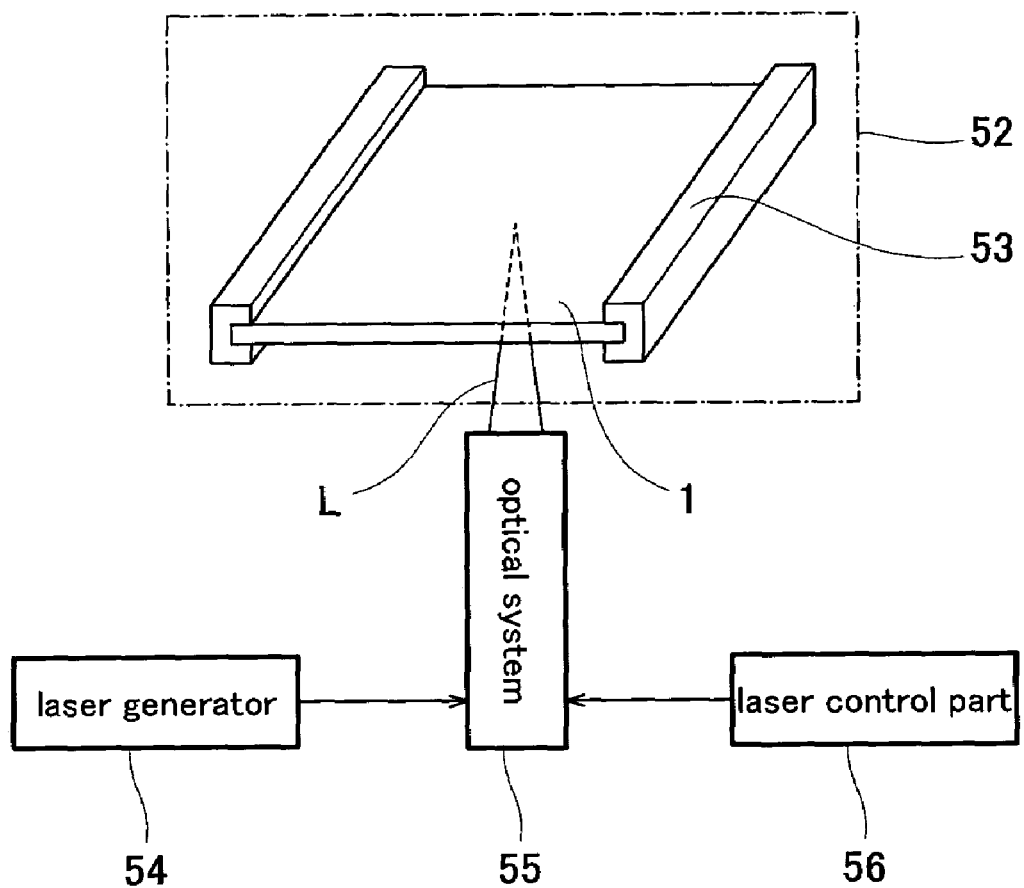
FIG. 9 is a block diagram illustrating a construction of a device for controlling movement of a fluid according to the first embodiment.

Next, one mode of a device for controlling movement for the purpose of controlling movement of a liquid in the flow channel 31 of the capillary chip 1 will be explained. FIG. 9 is a block diagram illustrating a device for controlling movement 51. The device for controlling movement 51 comprises a capillary chip attached part 52, a laser generator 54, an optical system 55 and a laser control part 56. Herein, the laser generator 54 and the optical system 55 are also referred to as a laser irradiation part, in combination. The device for controlling movement 51 is used after attaching the capillary chip 1 to the capillary chip attached part 52. The capillary chip attached part 52 has a guide member 53 for attaching, e.g., the capillary chip 1. Laser beam L emitted from the laser generator 54, and narrowed down by the optical system 55 is irradiated on the capillary chip 1. The laser control part 56 controls the optical system 55, and thus, irradiating position of the laser beam L is controlled through polarizing the laser beam L in the optical system 55. The laser control part 56 controls the laser beam L so that it is irradiated on the opening/closing part V1, and the opening/closing part V2 of the movement control part C1. Moreover, control with the laser control part 56 also enables irradiation while scanning the laser beam L, and further, it also enables concurrent irradiation on the adjacent multiple opening/closing parts V2 through adjusting the extent of narrowing of the laser beam L in the optical system 55.

Therefore, the method of controlling opening/closing of the opening/closing parts V1 and, V2, and the method of controlling movement of the movement control part C1 as described above can be performed by the device for controlling movement 51.

The device for controlling movement may be constructed to comprise a laser capable of irradiating multiple laser beams L at the same time. Also, it may be constructed to have driving means for driving the capillary chip 1 so that the irradiation of the laser beam L is perfected on an arbitrary position of the capillary chip 1.

Figure 10:
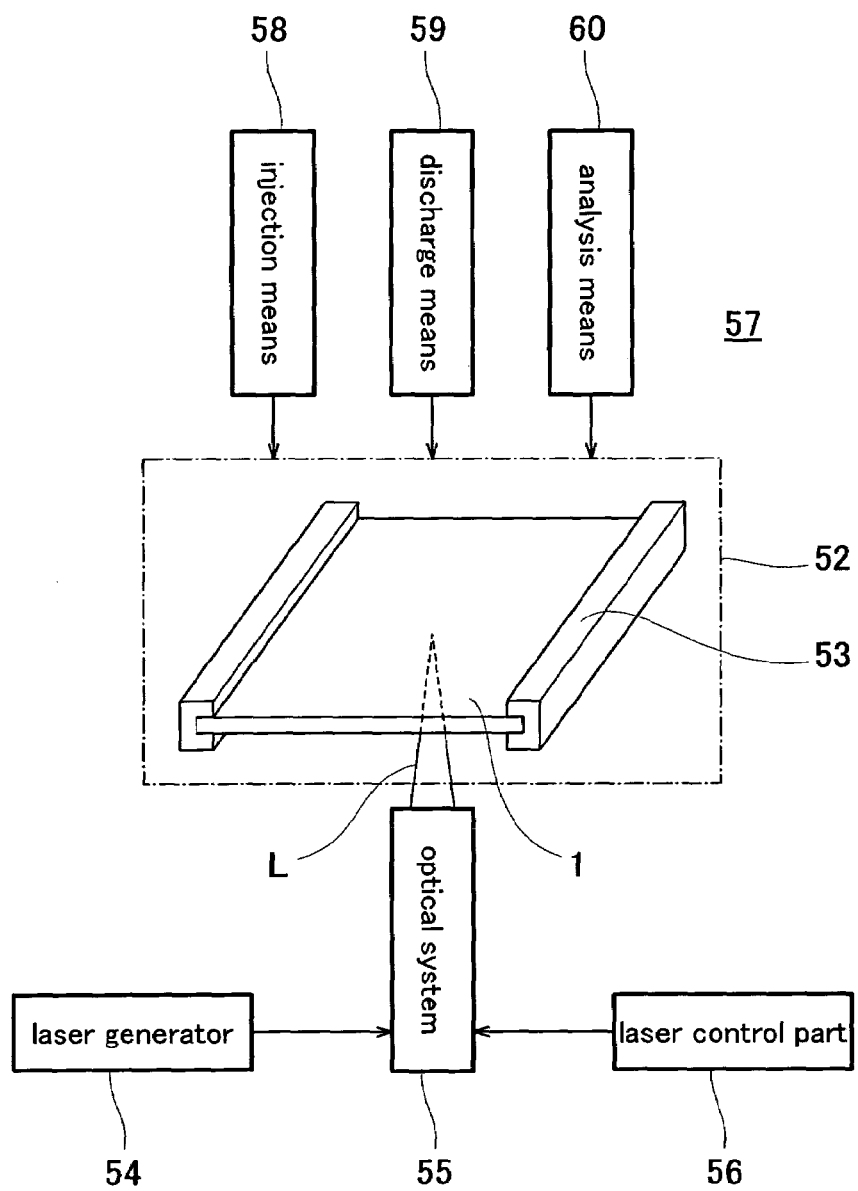
FIG. 10 is a block diagram illustrating a construction of a device for controlling movement of a fluid with a different mode from that illustrated in FIG. 9.

FIG. 10 is a block diagram illustrating a device for controlling movement 57 according to a mode which is different from that shown in FIG. 9. In FIG. 10, explanation of the same components as those in FIG. 9 is omitted by designating with the same reference numerals.

The device for controlling movement 57 illustrated in FIG. 10 is constructed to comprise injection means 58 capable of injecting the sample or the reagent into the sample inlet 21 or the reagent inlet 22 or 23, discharge means 59 capable of discharging effluent from the outlet 24, and analysis means 60 capable of analyzing as described above such as e.g., a microscope or the like, in the device for controlling movement 51 illustrated in FIG. 9. According to such a construction, injection of the sample and the reagent, the control of opening/closing, the control of movement, and the analysis can be conducted in single device.

Additionally, in the device for controlling movement illustrated in FIG. 9 and FIG. 10, a reaction in distinct capillary chip 1 can be analyzed by merely replacing the capillary chip 1 attached to the capillary chip attached part 52.

[First Method of Manufacturing Capillary Chip]

Figure 4A:
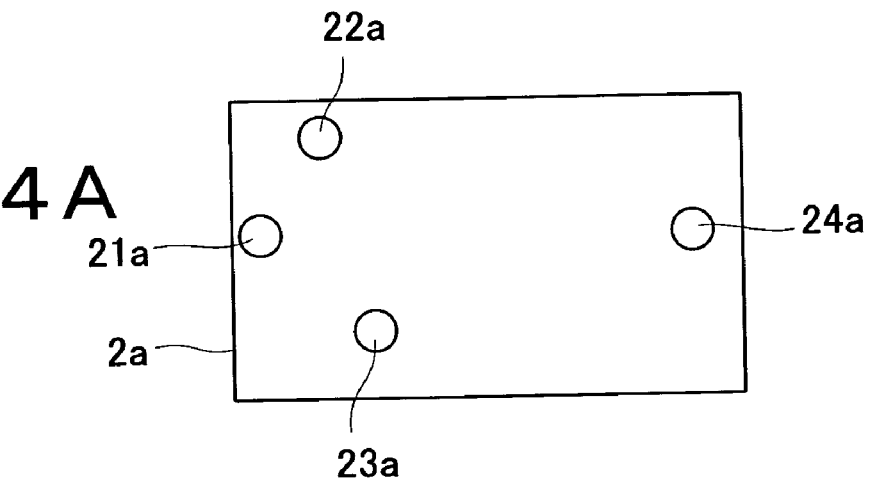
FIGS. 4A to 4C are each a view illustrating a first method of manufacturing a capillary chip.
Figure 4B:
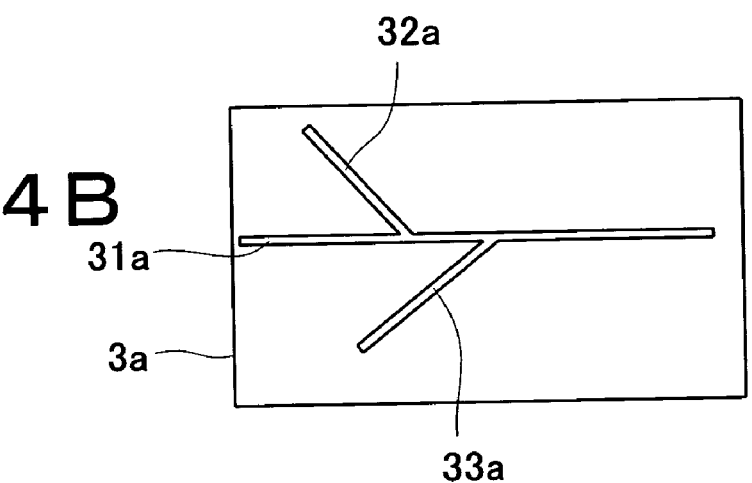
Figure 4C:
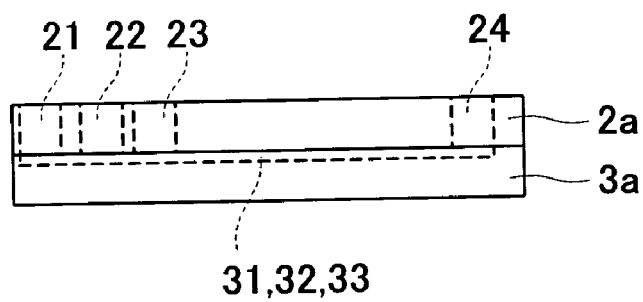

In this method, the capillary chip 1 is manufactured by bonding a main flat plate (flat plate for forming grooves) and a cover flat plate. FIG. 4A is a top view illustrating a cover flat plate 2a; FIG. 4B is a top view illustrating a main flat plate 3a; and FIG. 4C is a cross sectional view illustrating a vertical section of the capillary chip 1 manufactured by the method according to the present method of manufacture. The aforementioned vertical section is a section given by cutting the main flow channel 31 in a longitudinal direction.

As shown in FIG. 4B, on the surface of the main flat plate 3a are formed grooves 31a, 32a and 33a to be a flow channel. As shown in FIG. 4A, to the cover flat plate 2a are formed four through-holes 21a, 22a, 23a and 24a to be a sample inlet, a reagent inlet and an outlet, respectively. Then, as shown in FIG. 4C, the capillary chip 1 is manufactured by bonding the main flat plate 3a and the cover flat plate 2a such that the face of the main flat plate 3a having the formed grooves 31a, 32a and 33a comes on the inward side.

As the main flat plate 3a, a substrate having a layer which comprises a particular polymer composition (hereinafter, referred to as "polymer composition layer") on the surface thereof may be used. Details of such a polymer composition are similar to those of the polymer composition for forming the opening/closing part V1 as described above. Process of forming the polymer composition layer on the substrate is not limited, but it can be conducted by any of a number processes such as e.g., spray deposition, coating, dipping, gravure printing, rolling and the like.

More specifically, Intelimer® of cool off type (manufactured by Nitta Corporation), which is a thermosensitive adhesive tape having a substrate consisting of a PET film on which a layer comprising a polymer composition capable of causing first order melting transition is formed on the surface thereof, can be used as a material of the main flat plate 3a. Intelimer® of cool off type increases in the volume by heating from a temperature lower than the melting temperature range to a higher temperature, while it decreases in the volume by cooling from a temperature higher than the melting temperature range to a lower temperature. Among the aforementioned Intelimer® of cool off type, Intelimer® with a melting temperature range of approximately 30° C. or greater and 40° C. or less, and Intelimer® having the range of approximately 40° C. or greater and 50° C. or less and the like are suited as the material of the main flat plate 3a.

The grooves 31a, 32a and 33a are formed on the surface of the polymer composition layer. Thickness of the polymer composition layer is not particularly limited as long as it is greater than the depth of the grooves 31a, 32a and 33a. Whole of the main flat plate 3a may be also formed with the particular polymer composition. In this method, because the grooves are entirely formed with a polymer composition, the opening/closing part or the movement control part can be provided at any arbitrary site in the flow channel. In this instance, heating means such as e.g., a movable laser which can irradiate on an arbitrary site is preferably used as the heating means.

Moreover, the aforementioned polymer composition layer is also formed inside of the cover flat plate 2a herein. According to such a construction, entire circumferences of the flow channels 31, 32 and 33 formed by bonding the main flat plate 3a and the cover flat plate 2a are formed with the polymer composition. However, the construction is not limited thereto, but the cover flat plate 2a may be constructed so that the aforementioned polymer composition is not formed. In this instance, a part of the entire circumference of the flow channels 31, 32 and 33 has come to be formed with the polymer composition.

Substrate of the main flat plate 3a (i.e., part other than the polymer composition layer), and the cover flat plate 2a (part other than the polymer composition layer) can be manufactured with an inorganic material such as silicon or glass, or an organic polymer. In at least one of the substrate of the main flat plate 3a, and the cover flat plate 2a may be used a material having transparency on a wavelength of a light emitted from the heating means. For example, when the opening/closing part V1 or the movement control part C1 is heated with a laser, a laser light is irradiated from outside of the capillary chip 1. Therefore, it is necessary to allow the laser light to attain to the opening/closing part V1 and the movement control part C1 from outside, thereby requiring securement of transparency in the light path of the laser light.

The grooves 31a, 32a and 33a on the surface of the main flat plate 3a are formed by a process such as cutting processing, etching processing with a laser, or the like. The through-holes 21a, 22a, 23a and 24a of the cover flat plate 2a are formed by a process such as sonication processing or the like. The through-holes 21a, 22a and 23a of the cover flat plate 2a are formed at a position substantially corresponding to the uppermost stream position of the grooves 31a, 32a and 33a of the main flat plate 3a, respectively. The through-hole 24a is formed at a position substantially corresponding to the downmost stream position of the groove 31a. Then, the capillary chip 1 is formed by bonding the main flat plate 3a having the grooves 31a, 32a and 33a formed thereon, and the cover flat plate 2a having through-holes 21a, 22a, 23a and 24a such that the face having the grooves 31a, 32a and 33a comes on the inward side. The bonding of the main flat plate 3a with the cover flat plate 2a may be carried out by a process such as e.g., ultrasonic fusion, adhesion with an adhesive such as a hot melt adhesive or a UV adhesive or the like, cohesion with a cohesive agent, pressure welding with a double-faced tape, or the like.

As is illustrated in FIG. 4C, in the capillary chip 1, the grooves 31a, 32a and 33a shall become the flow channels 31, 32 and 33; the through-hole 21a shall become the sample inlet 21; the through-holes 22a and 23a shall become the reagent inlets 22 and 23; and the through-hole 24a shall become the outlet 24.

[Second Method of Manufacture of Capillary Chip]

Figure 5A:
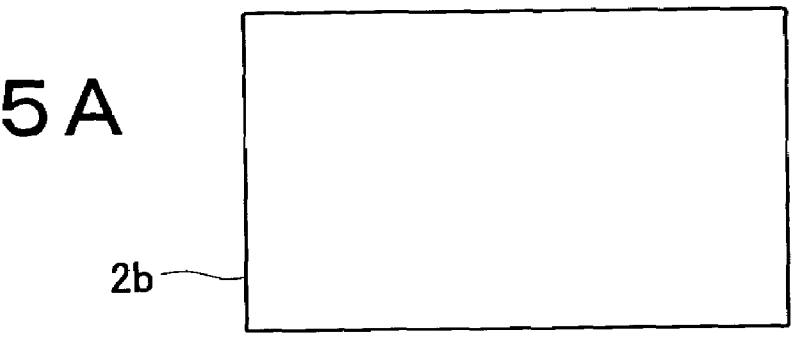
FIGS. 5A to 5C are each a view illustrating a second method of manufacturing a capillary chip.
Figure 5B:
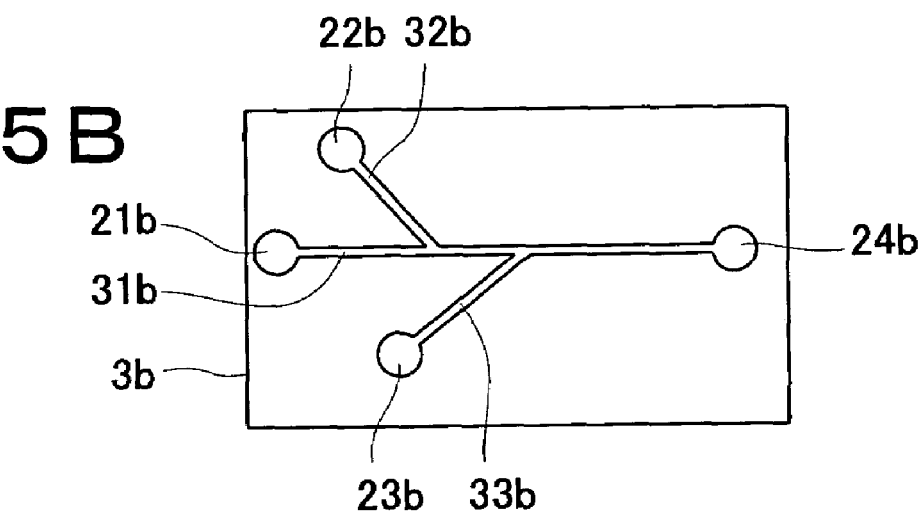
Figure 5C:
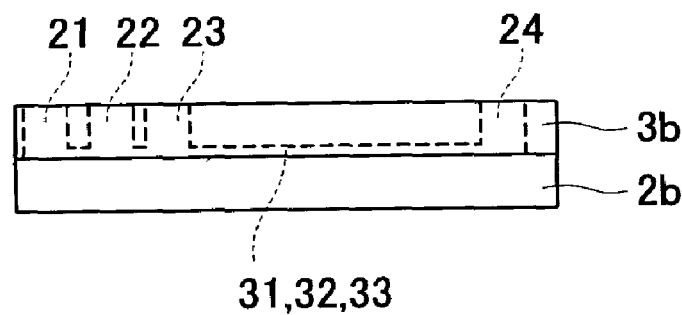

In this method, the capillary chip 1 is manufactured by bonding a main flat plate (flat plate for forming grooves) and a cover flat plate. FIG. 5A is a top view illustrating a cover flat plate 2b; FIG. 5B is a top view illustrating a main flat plate 3b; and FIG. 5C is a cross sectional view illustrating a vertical section of the capillary chip 1 manufactured by the method according to the present method of manufacture. The aforementioned vertical section is a section given by cutting the main flow channel 31 in a longitudinal direction.

As shown in FIG. 5B, on the surface of the main flat plate 3b are formed grooves 31b, 32b and 33b to be a flow channel. Further, through-holes 21b, 22b, 23b and 24b are formed to the main flat plate 3b. The through-holes 21b, 22b and 23b are formed at the uppermost stream position of the grooves 31b, 32b and 33b, respectively. The through-hole 24b is formed at the downmost stream position of the groove 31b.

Then, as shown in FIG. 5C, the capillary chip 1 is formed by bonding the main flat plate 3b and the cover flat plate 2b such that the face having the grooves 31b, 32b and 33b formed on the main flat plate 3b comes on the inward side.

The method of manufacture is similar to the first method of manufacture except that the grooves 31, 32 and 33, and through-holes 21, 22, 23 and 24 are formed on the identical main flat plate 3b. Also, as the main flat plate 3b and the cover flat plate 2b, any of those comprising the same material as those for the main flat plate 3a and the cover flat plate 2a used in the first method of manufacture can be employed. Therefore, because the grooves are entirely formed with a polymer composition also in this method, the opening/closing part or the movement control part can be provided at any arbitrary site in the flow channel.

As shown in FIG. 5C, in the capillary chip 1, the grooves 31b, 32b and 33b shall become the flow channels 31, 32 and 33; the through-hole 21b shall become the sample inlet 21; the through-holes 22b and 23b shall become the reagent inlets 22 and 23; and the through-hole 24b shall become the outlet 24.

[Third Method of Manufacture of Capillary Chip]

Figure 6A:
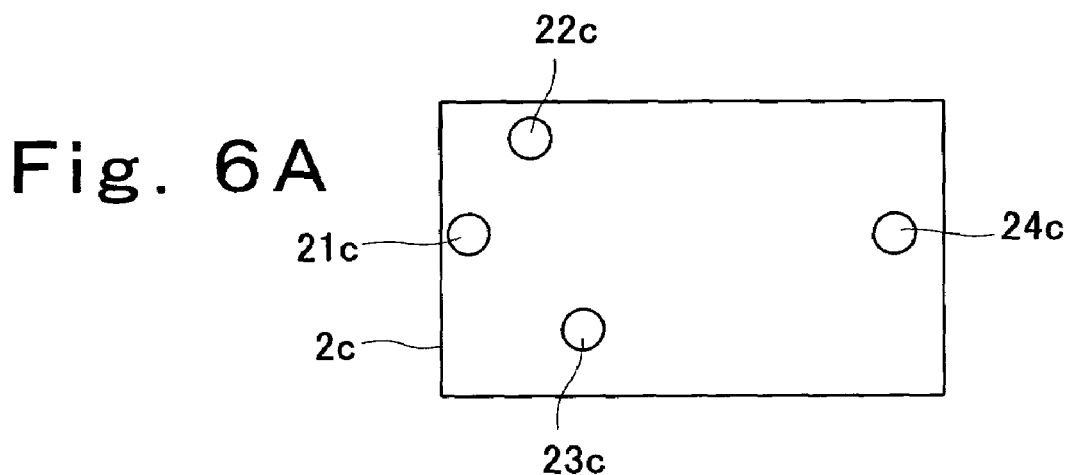
FIGS. 6A to 6D are each a view illustrating a third method of manufacturing a capillary chip.
Figure 6B:
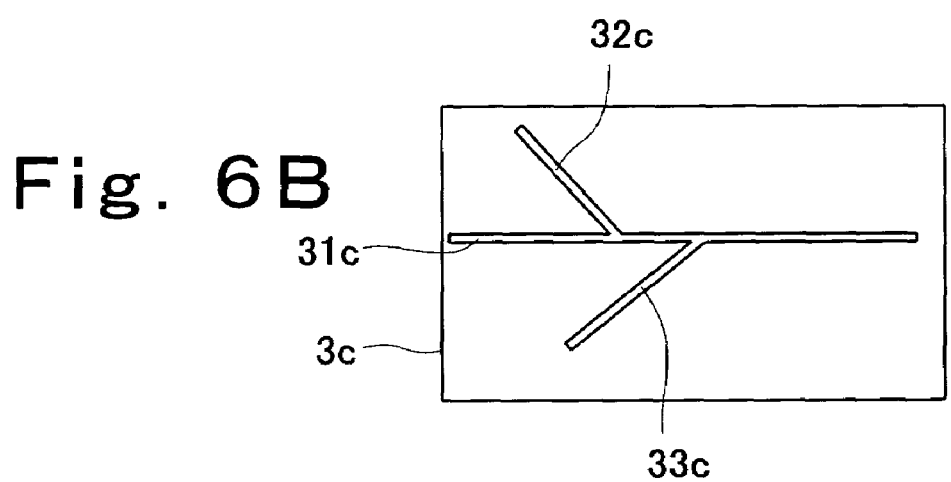
Figure 6C:
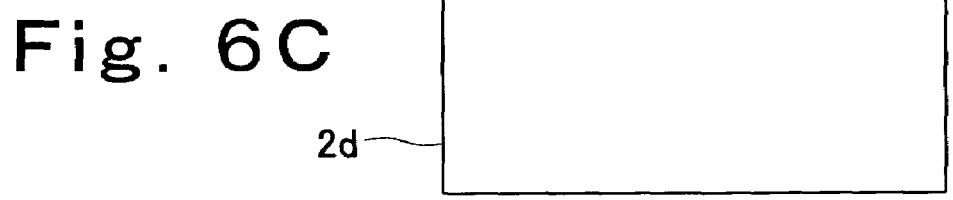
Figure 6D:
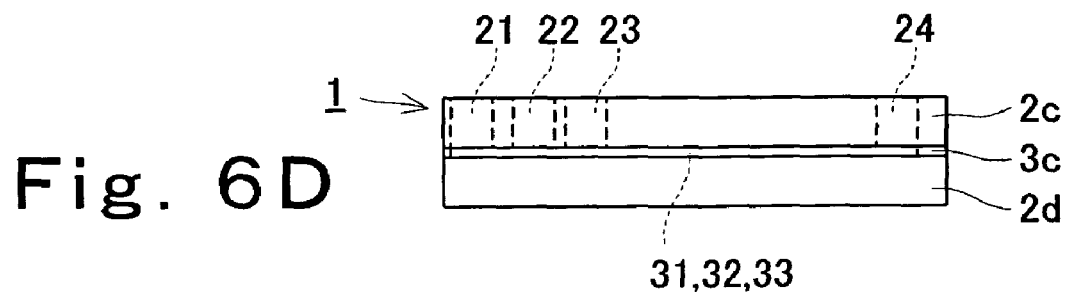

In this method, the capillary chip 1 is manufactured by bonding a main flat plate (flat plate for forming slits) and two cover flat plates. FIG. 6A is a top view illustrating a first cover flat plate 2c; FIG. 6B is a top view illustrating a main flat plate 3c; FIG. 6C is a top view illustrating a second cover flat plate 2d; and FIG. 6D is a cross sectional view illustrating a vertical section of the capillary chip 1 manufactured by the method according to the present method of manufacture. The aforementioned vertical section is a section given by cutting the main flow channel 31 in a longitudinal direction.

As shown in FIG. 6B, slits 31c, 32c and 33c to be flow channels are formed on a main flat plate 3c. The slits 31c, 32c and 33c pass through the main flat plate 3c from the front face to the reverse face. As shown in FIG. 6A, four through-holes 21c, 22c, 23c and 24c to be a sample inlet, reagent inlets, and an outlet, respectively, are formed on the first cover flat plate 2c. Then, as shown in FIG. 6D, the capillary chip 1 is manufactured by bonding the main flat plate 3c, the first cover flat plate 2c and the second cover flat plate 2d such that the main flat plate 3a is sandwich between the two cover flat plates 2c and 2d.

As the main flat plate 3b, a plate comprising a polymer composition is used. The polymer composition referred to herein is similar to that described above as the polymer composition for forming the opening/closing part V1. This method is similar to the first method of manufacture except that a flat plate which is similar to the main flat plate 3a in the first method of manufacture is formed by bonding the main flat plate 3c and the second cover flat plate 2d. Therefore, because the slits are entirely formed with a polymer composition also in this method, the opening/closing part or the movement control part can be provided at any arbitrary site in the flow channel. It is preferred that the polymer composition layer is formed on the inner face of the two cover flat plates 2c and 2d, because entire circumference of the flow channels 31, 32 and 33 consists of the polymer composition, but not limited to such a construction.

As shown in FIG. 6D, in the capillary chip 1, the slits 31c, 32c and 33c shall become the flow channels 31, 32 and 33; the through-hole 21c shall become the sample inlet 21; the through-holes 22c and 23c shall become the reagent inlets 22 and 23; and the through-hole 24c shall become the outlet 24.

Second Embodiment

[Construction of Capillary Chip]

Figure 7:
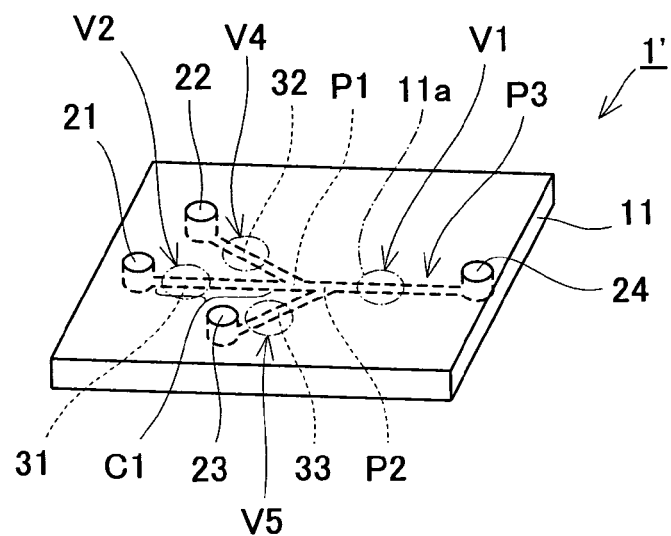
FIG. 7 is a perspective view schematically illustrating an external appearance of a capillary chip used in the second embodiment.

FIG. 7 is a perspective view schematically illustrating an external appearance of a capillary chip 1' used in this embodiment. As shown in FIG. 7, the capillary chip 1' comprises opening/closing parts V2, V4 and V5, having the same construction to the opening/closing part V1, through allowing the sample inlet 21 and the reagent inlets 22 and 23 to correspond to the vicinity of the upstream end of the flow channels 31, 32 and 33, respectively. The opening/closing part V2 also serves doubly as the opening/closing part of the movement control part C1. Other construction is similar to the construction of the capillary chip 1 of the first embodiment, therefore, explanation of the same components is omitted by designating with the same reference numerals.

[Method of Using Capillary Chip]

The capillary chip 1' can be used by a similar method to that of the capillary chip 1 in the first embodiment. In addition, by controlling the opening/closing of the opening/closing parts V2, V4 and V5, timing of initiating the movement, timing of terminating the movement, and the amount of movement of the sample injected into the sample inlet 21, and of the reagents injected into the reagent inlets 22 and 23 can be controlled.

Using device for controlling movement demonstrated in the first embodiment, the capillary chip 1' in this embodiment can also conduct the control of opening/closing, the control of movement, the analysis, and the like.

Third Embodiment

[Construction of Capillary Chip]

Figure 8A:
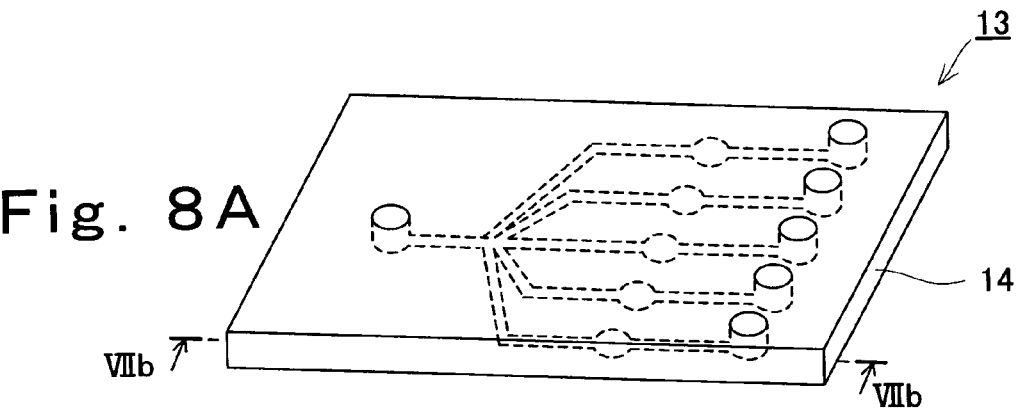
FIG. 8A is a perspective view schematically illustrating an external appearance of a capillary chip used in the third embodiment.
Figure 8B:
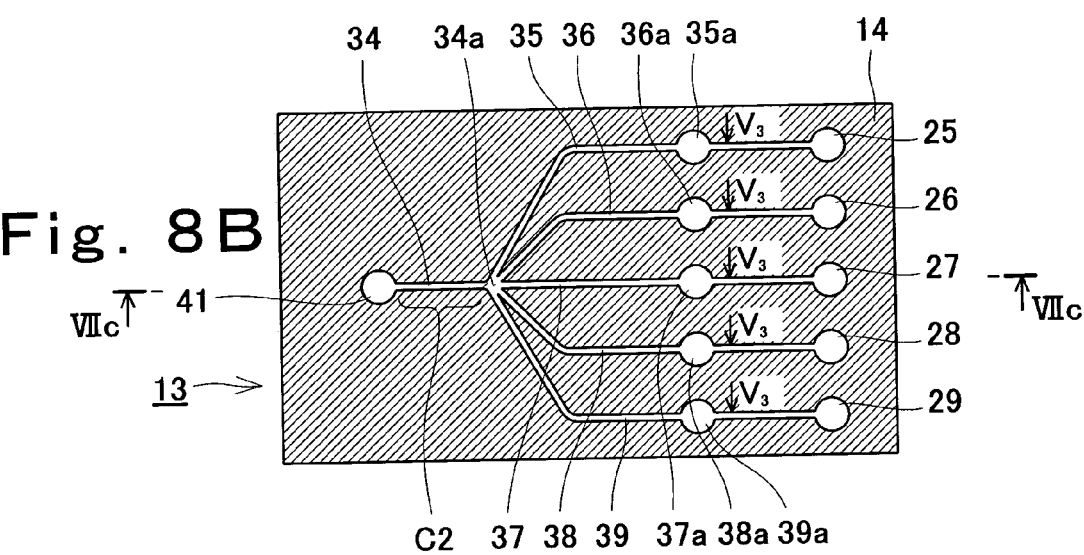
FIG. 8B is a cross sectional view showing a VIIb—VIIb section.
Figure 8C:
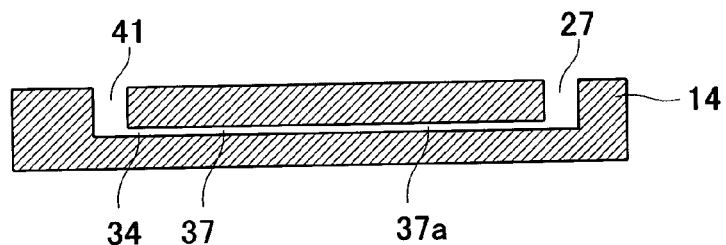
FIG. 8C is a cross sectional view showing a VIIc—VIIc section.

FIG. 8A is a perspective view schematically illustrating an external appearance of a capillary chip 13 used in this embodiment. FIG. 8B is a cross sectional view showing a VIIb—VIIb section in FIG. 8A, and FIG. 8C is a cross sectional view showing a VIIc—VIIc section in FIG. 8B. As shown in FIG. 8A to FIG. 8C, the capillary chip 13 comprises a substrate 14 having a rectangular top face on which a main flow channel 34, branch flow channels 35, 36, 37, 38 and 39, an inlet 41, and outlets 25, 26, 27, 28 and 29 are formed. Each of the flow channels 34, 35, 36, 37, 38 and 39 is constructed with a capillary. The main flow channel 34 joins to five branch flow channels 35, 36, 37, 38 and 39 at a junction 34a.

The main flow channel 34 has a movement control part C2 in the vicinity of the upstream end. Each of the branch flow channels 35, 36, 37, 38 and 39 has each of the reaction parts 35a, 36a, 37a, 38a and 39a having a circular top view and having a greater volume with respect to a unit length in the movement direction than other part, and an opening/closing part V3 on juxta downstream side of each of the reaction parts 35a, 36a, 37a, 38a and 39a. Each opening/closing part V3 corresponds to each of the outlets 25, 26, 27, 28 and 29.

Because the capillary chip 13 of this embodiment differs from the capillary chip 1 in the first embodiment only in terms of its design of the flow channel, detailed description of each component is omitted. Construction of the opening/closing part V3 and method of the control thereof are similar to those of the opening/closing part V1 in the first embodiment. Construction of the movement control part C2 and method of the control thereof are similar to those of the movement control part C1 in the first embodiment.

[Method of Using Capillary Chip]

Method of using the capillary chip 13 will be explained below. A cell suspension in a medium is injected from the inlet 41, and liquid delivery of the aforementioned suspension is conducted utilizing the pumping function carried out by the movement control part C2, to the reaction parts 35a, 36a, 37a, 38a and 39a of the branch flow channels 35, 36, 37, 38 and 39, respectively. After each of the reaction parts 35a, 36a, 37a, 38a and 39a is filled with the aforementioned suspension, the opening/closing part V3 provided on each of the branch flow channels 35, 36, 37, 38 and 39 is turned into the closed state.

After leaving to stand in this state for 2 days, the cells are cultured in the reaction layers 35a, 36a, 37a, 38a and 39a. Thereafter, the opening/closing part V3 of each of the branch flow channels 35, 36, 37, 38 and 39 is turned into the open state, and a reagent solution containing a first medicinal drug candidate compound dissolved therein is injected from the inlet 41. Utilizing the pumping function carried out by the movement control part C2, liquid delivery of the reagent solution described above is conducted to each of the reaction parts 35a, 36a, 37a, 38a and 39a. Then, the opening/closing part V3 is turned into the closed state at the time when each of the reaction parts 35a, 36a, 37a, 38a and 39a is filled with the reagent described above.

Thereafter, cell toxicity, influence on the cell or the like of the first medicinal drug candidate compound is analyzed by observing the reaction parts 35a, 36a, 37a, 38a and 39a of the capillary chip 13 with a microscope. As the cell described above, an adherent cell is preferably used because almost the cells do not flow out from the reaction layers 35a, 36a, 37a, 38a and 39a even though liquid delivery of the reagent is conducted after the culture since the adherent cells adhere on the reaction layer.

In the embodiment described above, an opening/closing part may be provided at an upstream end of each of the branch flow channels 35, 36, 37, 38 and 39 which are branched, and may conduct liquid delivery of the reagent solution of different medicinal drug candidate compounds to each of the reaction layers 35a, 36a, 37a, 38a and 39a so that cell toxicity or the like of the multiple reagents may be concomitantly analyzed. In this instance, sort of the reagents subjected to the liquid delivery to each of the reaction parts 35a, 36a, 37a, 38a and 39a may be controlled by, for example, allowing only one flow channel to have a valve at the upstream end in the open state, while allowing other flow channels to have the opening/closing parts in the closed state, for each reagent.

Using the device for controlling movement demonstrated in the first embodiment, the capillary chip 13 according to this embodiment can also conduct the control of opening/closing, the control of movement, the analysis and the like.

According to the first to third embodiments, the control of movement and the control of opening/closing in the capillary can be achieved by a simple process to change the temperature of the opening/closing part at the capillary chip. Moreover, since the capillary is formed on the surface or inside of the layer comprising a polymer composition, an arbitrary site can be selected as the opening/closing part.

In addition, properties of the sample and the reagent are not affected upon the control of movement and the control of opening/closing by the method according to the embodiment as described above. Furthermore, means required for conducting the control as described above can be constructed with compact ones which enable keeping quiet.

From the foregoing descriptions, numerous improvements and other embodiment of the present invention will be apparent to persons skilled in the art. Accordingly, the foregoing descriptions should be construed as merely illustrative examples, which are provided for the purpose of teaching persons skilled in the art of best embodiment for carrying out the present invention. Without departing from the spirit of the present invention, details of the structure and/or function thereof can be substantially altered.

The method of moving a fluid according to the present invention is useful in moving a liquid such as a reagent, a sample or the like in micro chips for use in a medical diagnosis or in micro chips for use in detecting responsiveness of a drug.

Additionally, the method of moving a fluid according to the present invention can be used in micro TAS in which analysis is conducted using a micro chip. For example, it can be used in micro TAS for analyzing a biological sample such as blood, spinal fluid, saliva, urine or the like.

The method of moving a fluid according to the present invention is useful as a method to be applied to capillary chips for disposable use, in particular, because desired control of opening/closing and control of movement can be conducted in micro chips with a simple construction.

What is claimed is:

1. A method of moving a fluid in a capillary using a capillary chip having a layer comprising a polymer composition and a capillary formed on the surface or inside of said layer comprising a polymer composition, wherein
    said capillary has a movement control part, and said movement control part comprises multiple and sequential opening/closing parts;
    said opening/closing part blocks movement of the fluid that flows in said capillary by increase in the volume of said polymer composition to result in the closed state, while it permits movement of the fluid that flows in said capillary by decrease in the volume of said polymer composition to result in the open state; and
    said method of moving the fluid comprises:
    step (a) of switching said multiple opening/closing parts from the open state to the closed state sequentially in a movement direction by changing the temperature of said polymer composition in said movement control part, thereby moving the fluid in said capillary.

2. The method of moving the fluid according to claim 1 wherein the step (a) is conducted repeatedly more than once.

3. The method of moving the fluid according to claim 2 which comprises after each step (a):
step (b) of, while keeping the closed state of one or more opening/closing parts positioned from the downstream end along the movement direction, switching other opening/closing part from the closed state to the open state by changing the temperature of said polymer composition in said movement control part; and
step (c), following the step (b), of switching the opening/closing part from the closed state in the step (b) to the open state,
wherein the next step (a) is initiated substantially concomitantly to the step (c).

4. The method of moving the fluid according to claim 1 which further comprises:
step (d) of blocking movement of the fluid that flows in said capillary through changing the temperature of said polymer composition in said opening/closing part to turn said opening/closing part into the closed state; and
step (e) of permitting movement of the fluid that flows in said capillary through changing the temperature of said polymer composition in said opening/closing part to turn said opening/closing part into the open state.

5. The method of moving the fluid according to claim 1 wherein said polymer composition increases in the volume upon elevation of the temperature, and decreases in the volume upon lowering of the temperature.

6. The method of moving the fluid according to claim 1 wherein said polymer composition decreases in the volume upon elevation of the temperature, and increases in the volume upon lowering of the temperature.

7. The method of moving the fluid according to claim 1 wherein said polymer composition comprises a side chain-crystalline recurring unit derived from an acrylate or methacrylate ester, and a side chain-noncrystalline recurring unit derived from an acrylate or methacrylate ester.

8. The method of moving the fluid according to claim 1 wherein said capillary is formed on the surface of said layer, and a cover flat plate coheres on the surface of said layer in said capillary chip.

9. The method of moving the fluid according to claim 1 wherein said capillary chip further comprises a fluid inlet and a fluid outlet connected to said capillary.

10. The method of moving the fluid according to claim 1 wherein said opening/closing part of said movement control part is sequentially heated in the movement direction in the step (a) to switch said opening/closing part from the open state to the closed state in the movement direction.

11. The method of moving the fluid according to claim 10 wherein said heating is executed by irradiating a laser in the step (a).

12. The method of moving the fluid according to claim 3 wherein said opening/closing part is switched from the closed state to the open state by air-cooling of said opening/closing part in the step (b) and the step (c).

13. The method of moving the fluid according to claim 1 wherein said polymer composition alters said volume by the first order melting transition thereof.

14. The method of moving the fluid according to claim 12 wherein the first order melting transition of said polymer composition is caused at 80° C. or lower.

15. The method of moving the fluid according to claim 1 wherein cross sectional area of said capillary is 10000 $\mu m^2$ or greater and 250000 $\mu m^2$ or less.

16. The method of moving the fluid according to claim 1 wherein said capillary chip has multiple fluid inlets that are connected to said capillary, and said capillary has multiple opening/closing parts so as to correspond to each fluid inlet.

17. A device for controlling movement of a fluid which comprises a capillary chip attached part, a laser irradiation part and a laser control part, wherein
a capillary chip can be attached to said capillary chip attached part;
said capillary chip has a layer comprising a polymer composition, and a capillary formed on the surface or inside of said layer comprising a polymer composition;
said capillary comprises a movement control part, and said movement control part comprises multiple and sequential opening/closing parts;
said opening/closing part blocks movement of the fluid that flows in said capillary by increase in the volume of said polymer composition to result in the closed state, while it permits movement of the fluid that flows in said capillary by decrease in the volume of said polymer composition to result in the open state;
said laser irradiation part can irradiate a laser on the capillary chip attached to said capillary attached part; and
said laser control part can control a position where a laser is irradiated on the capillary chip attached to said capillary attached part by said laser irradiation part, and said opening/closing part is switched from the open state to the closed state sequentially in a movement direction by irradiating said opening/closing part sequentially in the movement direction thereby moving the fluid in said capillary.

* * * * *